United States Patent [19]

Lin et al.

[11] Patent Number: 5,019,371

[45] Date of Patent: May 28, 1991

[54] NOVEL X-RAY CONTRAST AGENTS, COMPOSITIONS AND METHODS

[75] Inventors: Youlin Lin, Chesterfield; Rebecca A. Wallace, Manchester; David H. White, Florissant, all of Mo.

[73] Assignee: Mallinckrodt Medical, Inc., St. Louis, Mo.

[21] Appl. No.: 616,495

[22] Filed: Nov. 21, 1990

[51] Int. Cl.$^5$ .................... A61K 49/04; C07C 233/05
[52] U.S. Cl. ................................ 424/5; 564/165
[58] Field of Search ........................ 424/5; 564/165

[56] References Cited

U.S. PATENT DOCUMENTS

| | | | |
|---|---|---|---|
| 4,021,481 | 5/1977 | Almen et al. | 424/5 X |
| 4,307,072 | 12/1981 | Smith | 564/165 X |
| 4,352,788 | 10/1982 | Felder et al. | 424/5 |

*Primary Examiner*—John S. Maples
*Attorney, Agent, or Firm*—Rita E. Downard; Roy J. Klostermann

[57] ABSTRACT

The compound N-(2,3-dihydroxypropyl)-5-[N-(2-hydroxyethyl)-glycolamido]-N'-methyl-2,4,6-triiodoisophthalamide and similar such compounds may be used as x-ray contrast agents which are water-soluble, safe and in an aqueous solution are non-viscous. Methods of preparing N-(2,3-dihydroxypropyl)-5-[N-(2-hdyroxyethyl)glycolamido]-N'-methyl-2,4,6-triiodoisophthalamide are provided.

6 Claims, No Drawings

NOVEL X-RAY CONTRAST AGENTS, COMPOSITIONS AND METHODS

BACKGROUND OF THE INVENTION

This invention relates to x-ray contrast agents and, more particularly, to novel nonionic x-ray contrast agents, radiological compositions containing such agents and methods for X-ray visualization utilizing such compositions.

Nonionic contrast agents for intravascular and central nervous system visualization are complex molecules. As is known, the iodine in the molecule provides opacification to the x-rays. The remainder of the molecule provides the framework for transport of the iodine atoms. However, the structural arrangement of the molecule is important in providing stability, solubility and biological safety in various organs. A stable carbon-iodine bond is achieved in most compounds by attaching it to an aromatic nucleus. An enhanced degree of solubility as well as safety is conferred on the molecule by the addition of suitable solubilizing and detoxifying groups.

Futhermore, several features are desirable for intravascular and central nervous system nonionic agents. These include (1) maximum opacity to x-rays, (2) biological safety, (3) high water solubility, (4) chemical stability, (5) low osmolality, (6) no ionic charge, and (7) low viscosity.

There is a continuing need for nonionic contrast agents which meet all or substantially all the foregoing criteria. In addition to preparing the stable, watersoluble and safe agents, the recent studies have been in the development of low osmolality agents. Studies have shown that high osmolality can be correlated with many of the undesirable physiologic adverse reactions after the x-ray contrast medium intravenous injection, e.g. neausea, vomiting, heat and pain. The most recent major improvement is the introduction of low osmolar, nonionic agents, such as iopamidol, iohexol and ioversol. These new low osmolar agents provide patient comfort by causing less nausea and vomiting on intravenous injection and much less pain on peripheral arterial injection.

SUMMARY OF THE INVENTION

Among the several objects of the invention may be noted the provision of novel nonionic contrast agents, radiological compositions and methods for x-ray visualization; and the provision of such agents which are substantially non-toxic and meet the other criteria desired for nonionic contrast agents. Other objects and features will be in part apparent and in part pointed out hereinafter.

Briefly, the present invention is directed to compounds of the formula:

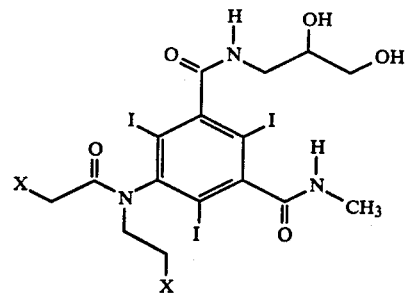

wherein the X groups may be the same or different selected from a group consisting of hydroxy and alkoxy, wherein the alkoxy group contains from 1 to 6 carbon atoms, such as for example methoxy, to reduce lipophilicity.

The invention is specifically directed to the compound N-(2,3-dihydroxypropyl)-5-[N-(2-hydroxyethyl)glycolamido]-N'-methyl-2,4,6-triiodoisophthalamide. The invention is also directed to radiological compositions containing such a compound and methods for utilizing such a compound in x-ray visualization.

DESCRIPTION OF THE PREFERRED EMBODIMENTS

In accordance with the present invention, it has now been found that compounds of the formula set out above are suitable for use as nonionic x-ray contrast agents. More specifically in the practice of the invention, the compound N-(2,3-dihydroxypropyl)-5-[N-(2-hydroxyethyl)glycolamido]-N'-methyl-2,4,6-triiodoisophthalamide may be used as a nonionic x-ray contrast agent. This compound is water-soluble, safe (i.v. $LD_{50}$ in mice is 16.1 gI/Kg) and its aqueous solution is non-viscous (6.3 cps at 25° as a 32% I solution). Particularly, it exhibits remarkably low osmolality (400 mOsm/Kg as a 32% I solution). This agent may be used in various radiographic procedures including those involving cardiography, coronary arteriography, aortography, cerebral and peripheral angiography, orthography, intravenous pyelography and urography.

In further accordance with the present invention, radiological compositions may be prepared containing the aforementioned compound as an x-ray contrast agent together with a pharmaceutically acceptable radiological vehicle.

Pharmaceutically acceptable radiological vehicle's include those that are suitable for injection such as aqueous buffer solutions; e.g., tris(hydroxymethyl) amino methane (and its salts), phosphate, citrate, bicarbonate, etc., sterile water for injection, physiological saline, and balanced ionic solutions containing chloride and/or bicarbonate salts of normal blood plasma cations such as Ca, Na, K and Mg. Other buffer solutions are described in Remington's Practice of Pharmacy, Eleventh Edition, for example on page 170. The vehicles may contain a chelating amount, e.g., a small amount, of ethylenediamine tetraacetic acid, the calcium disodium salt, or other pharmaceutically acceptable chelating agent The concentration of the x-ray contrast agent of the present invention in the pharmaceutically acceptable vehicle, for example an aqueous medium, varies with the particular field of use. A sufficient amount is present to provide satisfactory x-ray visualization. For example, when using aqueous solutions for angiography, the concentration of iodine is generally 140–400 mg/ml and the dose is 25–300 ml.

The radiological composition is administered so that the contrast agent remains in the living animal body for about 2 to 3 hours, although both shorter and longer residence periods are normally acceptable. Thus, N-(2,3-dihydroxypropyl)-5-[N-(2-hydroxyethyl)-glycolamido]-N'-methyl-2,4,6-triiodoisophthalamide may be formulated for vascular visualization conveniently in vials or ampoules containing 10 to 500 ml. of an aqueous solution.

The radiological compositions of the invention may be used in the usual way in x-ray procedures. For example, in the case of selective coronary arteriography, a sufficient amount of the radiological composition to provide adequate visualization is injected into the coronary system and then the system is scanned with a suitable device such as a fluoroscope.

The compound N-(2,3-dihydroxypropyl)-5-[N-(2-hydroxyethyl)-glycolamido]-N'-methyl-2,4,6-triiodoisophthalamide and the intermediates therefor may be prepared in accordance with the procedures set out below. All temperature designations are in degrees centigrade.

The following examples illustrate the practice of the invention.

EXAMPLE I

N-(2,3-dihydroxypropyl)-5-[N-(2-hydroxyethyl)-glycolamido]-N'-methyl-2,4,6-triiodoisophthalamide A. Preparation of 5-amino-3-methylcarbamoyl-2,4,6-triiodobenzoyl chloride (2)

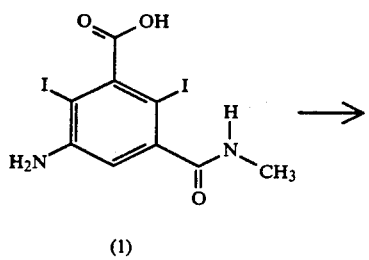

(1)

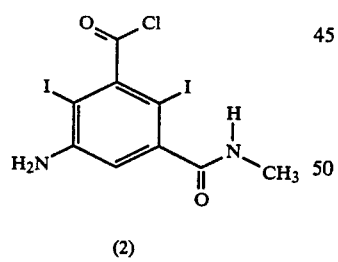

(2)

The flask was charged with thionyl chloride (600 ml, 978.6 g, 8.23 mol) and 5-amino-3-methylcarbamoyl-2,4,6-triiodobenzoic acid (320 g, 0.56 mol) was added in portions with stirring. The mixture was refluxed for one hour and an additional 100 ml of thionyl chloride was added. Refluxing was continued for 1.5 hours (total reflux time: 2.5 hours) until TLC indicated that the reaction was complete. Thionyl chloride was removed by vacuum distillation (30° C., 75 mmHg) until the consistency of the residue was pasty. The remaining traces of thionyl chloride were removed by three consecutive vacuum codistillations with 200 ml of THF. The resulting yellow paste was dissolved in 600 ml of THF and immersed in an ice bath while 500 ml of saturated NaCl was added. The pH of the aqueous layer (<1) was adjusted to approximately 6.9 with solid sodium carbonate (173 g, 1.63 mol) The mixture was filtered and the filter cake was washed with 200 ml of THF. The wash was combined with the mother liquor which was then allowed to separate into two layers. The organic layer was washed with 200 ml of saturated NaCl, the aqueous layer with 150 ml THF: the organic layers were combined and dried over 180 g of calcium chloride beads for one hour. The solution was concentrated to a volume of 400 ml and stirred with 200 ml of dry toluene for 16 hours. The creamy white solid thus formed was filtered, washed with 2×100 ml of dry cold toluene and dried under vacuum to give 228 g of product 2 (0.39 mol, 69%) as a pale yellow solid. $^{13}$C NMR (75.5 MHz, DMSO, ref. DMSO at 39.5 ppm): 170.2, 150.4, 148.9, 148.7, 83.0, 75.3, 70.1, 25.8. TLC: One spot (EtOAc/MeOH/HOAc, 10/5/1).

B. Preparation of 5-Acetoxyacetamido-3-methylcarbamoyl2,4,6-triiodobenzoyl chloride (3)

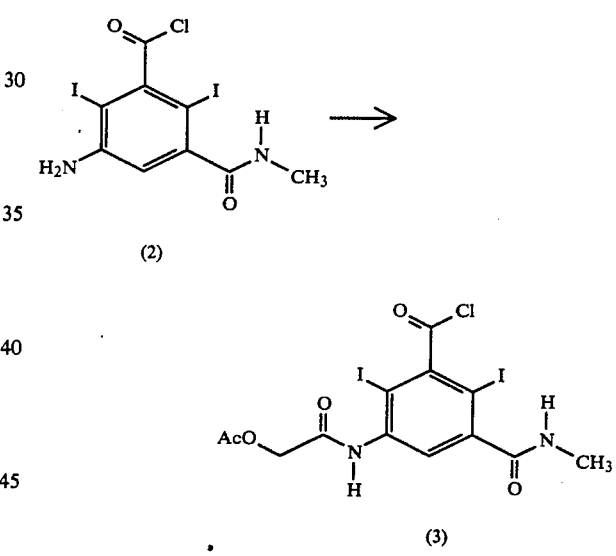

To a slurry of (2) (170 g, 0.29 mol) in 350 ml of N,N-dimethylacetamide (DMAc) was added 4-dimethylaminopyridine (DMAP) (1.86 g, 0.015 mol). The mixture was cooled to 0° C. and acetoxyacetyl chloride (62 ml, 78.6 g, 0.58 mol) was added dropwise, keeping the temperature <5° C. The mixture was stirred at 30° C. for 16 hours. The reaction mixture containing the solid white product was immersed in an ice bath for 2 hours, filtered, stirred with cold THF (1100 ml) for 1 hour, filtered and dried under vacuum for 2 days to give 190 g of product 3 (0.30 mol, 95%) as a white solid. $^{13}$C NMR (75.5 MHz, DMSO, ref. DMSO at 39.5 ppm): 170.6, 170.2, 169.9, 166.1, 166.0, 151.7, 149.8, 143.6, 143.5, 103.4, 97.0, 88.8, 62.4, 26.0, 20.6.

C. Preparation of N(2,3-dihydroxypropyl)-5-acetoxyacetamido-N'-methyl-2,4,6-triiodoisophthalamide

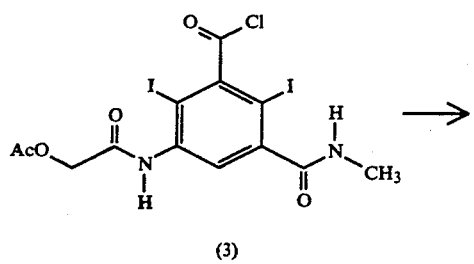

(3)

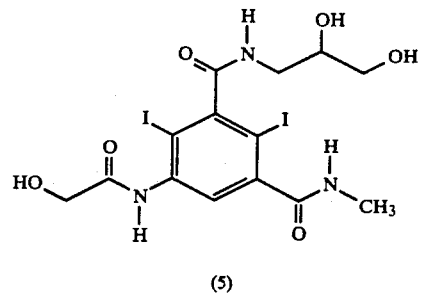

(5)

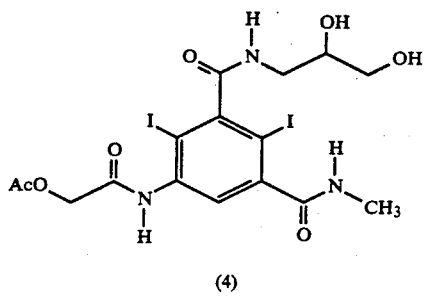

(4)

A solution of 3-amino-1,2-propanediol (APD) (36 g, 0.40 mol) in 100 ml dry DMAc was added dropwise to a slurry of (3) (200 g, 0.29 mol) and sodium carbonate (42 g, 0.40 mol) in 450 ml of dry DMAc, keeping the temperature at 25° C. with the application of an ice bath. Following the addition, the mixture was stirred at 35° C. for 22 hours.

Because a trace of starting material was still present, 4.2 g (0.04 mol) of Na₂CO₃ and 3.6 g (0.04 mol) of APD in 40 ml of DMAc were added. This mixture was stirred at 35° C. for 3.5 hours, at which time the reaction was complete. Approximately 450 g of DMAc was removed by rotary evaporation; the remaining oil was added dropwise to 1000 ml of acetone immersed in an ice bath, with stirring. After standing for 4.5 hours, the resultant solid was filtered, washed with 3×200ml of hexane, and dried under vacuum for 2.5 days to give 153 g of product 4 (0.21 mol, 71%) as an off-white powder (one spot by TLC, CHCl₃/MeOH:75/25).

D. Preparation of N-(2,3-dihydroxypropyl)-5-glycolamido-N'-methyl-2,4,6-triiodoisophthalamide (5)

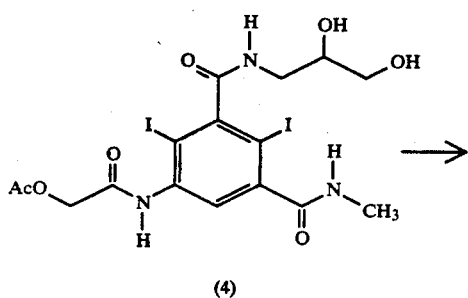

(4)

To a slurry of (4) (100 g, 0.13 mol) in 800 ml of MeOH was added 200 ml of 1.0N NaOH (8.0 g, 0.2 mol) as a steady stream over a 5 minute period. The solution was allowed to stir 16 hours. The pH (10.8) was adjusted to 7.0 with conc. HCl, and the solvents were removed by rotary evaporation to leave a cream colored paste. After stirring with 200 ml of cold water for 10 minutes, the solid product was filtered, washed with 2×300 ml of cold water, and dried in a vacuum desiccator for 24 hours to give 59 g of product 5 (0.08 mol, 63%) as a white solid.

¹³C NMR (75.5 MHz, DMSO, ref. DMSO at 39.5 ppm): 170.9, 170.4, 170.1, 150.7, 150.4, 143.3, 99.3, 90.3, 90.28, 70.1, 64.0, 61.9, 42.6, 25.9. One spot by TLC (CHCl₃/MeOH, 75/25).

E. Preparation of N-(2,3-diacetoxypropyl)-5-acetoxyacetamido-N'-methyl-2,4,6-triiodoisophthalamide (6)

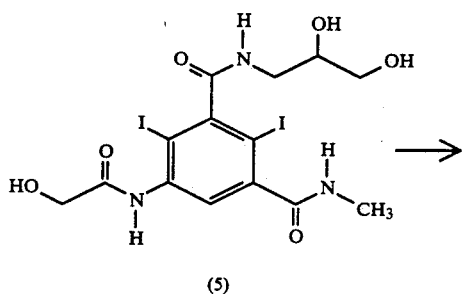

(5)

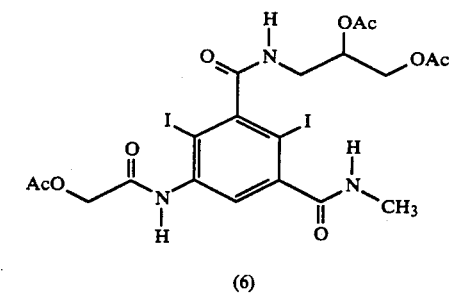

(6)

4-Dimethylaminopyridine (0.42 g, 0.0035 mol) was added to a slurry of (5) (52 g, 0.074 mol) in 140 ml of dry DMAc. An ice bath was applied, and acetic anhydride (35 ml, 37 g, 0.37 mol) was added at such a rate as to maintain the temperature below 10° C. The ice bath was removed, and the mixture was stirred at 45° C. for 4.5 hours, at which time an additional 14 ml (14.8 g, 0.15 mol) of acetic anhydride was added, and the solution was stirred at 45° C. for 16 hours. The resultant pale yellow solution which tested pure by TLC was stripped to an off-white foam (68 g), which was used as is in the following reaction. ¹³C NMR (75.5 MHz, DMSO, ref. DMSO at 39.5 ppm): 171.5, 170.6, 170.4, 170.0, 169.9, 168.4, 151.9, 151.2, 143.0, 100.2, 99.9, 69.7, 69.6, 64.5, 63.0, 25.8, 21.3, 21.0, 20.5, 20.2. One spot by TLC (CHCl₃/MeOH, 90/10).

F. Preparation of N-(2,3-diacetoxypropyl)-5-[N-(2-acetoxyethylethyl)acetoxyacetamide]-N'-methyl-2,4,6-triiodoisophthalamide (7)

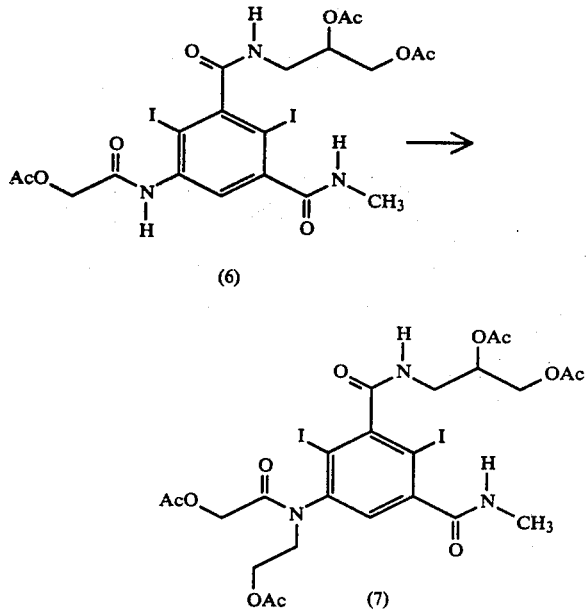

A slurry was formed by adding K₂CO₃ (18.35 g, 0.133 mol) to a solution of (6) (47.4 g, 0.057 mol) in 40 ml of DMSO. Bromoethylacetate (11.0 ml, 16.58 g, 0.099 mol) was added in one portion and the reaction mixture was stirred at 40° C. for 16 hours. At this point, 5.64 g (0.04 mol) K₂CO₃ and 5.64 ml (0.03 mol) bromoethylacetate were added and the mixture was stirred at 40° C. for 7 more hours, then at room temperature (~22° C.) four days. The additions were repeated (identical quantities), the mixture was stirred at 40° C. for 7 hours, and then at room temperature for 16 hours. The brown gum (58 g) of crude product (7) obtained after filtration followed by concentration was carried on to the next step without purification.

G. Preparation of N-(2,3-dihydroxypropyl)-5-[N-(2-hydroxyethyl-glycolamido]-N'-methyl-2,4,6-triiodoisophthalamide (8) (MP-871)

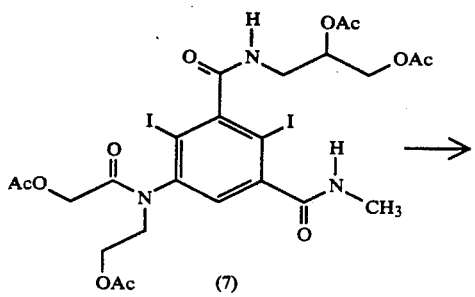

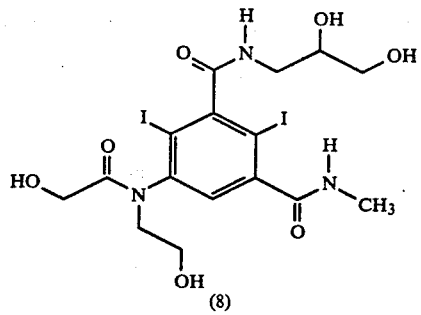

To a solution of the gum (containing (7)) above in 225 ml of MeOH was added dropwise a methanolic solution of sodium methoxide (prepared from 2.7 g, 0.068 mol of sodium metal and 225 ml MeOH) over a 30 minute period, keeping the temperature below 0° C. with an isopropanol-dry ice bath. The reaction was stirred at −5° to 0° C. for 2.5 hours, the pH was adjusted to 4.0 with conc. HOAc, and the solution was concentrated to a gum (52.4 g). Two consecutive preparative HPLC treatments yielded 19 g of a white glassy solid, 98.1% pure by HPLC. The solid was dissolved in approximately 400 ml of water and stirred with 0.38 g of activated charcoal at 60° C. for 2 hours, then at room temperature for 16 hours. The solution was filtered and passed through a column of amberlite IR-458 and IR-120 ion exchange resins (10 ml of each, Rohm and Haas Company). The water was evaporated to give 15 g of product 8 (0.02 mol) as a white glassy solid.

HPLC: 99.9 area %, one peak with a tailing shoulder, 31.5 minutes: 1.7 ml/min: H₂O/MeOH:98/2; ODS packing.

¹³C NMR (75.5 MHz, DMSO, ref. DMSO at 39.5 ppm): 171.8, 71.6, 170.4, 170.1, 170.0, 151.9, 152.0, 151.9, 151.7, 145.6, 100.7, 100.5, 100.2, 92.4, 70.4, 70.3, 70.0, 64.1, 64.0, 61.8, 58.6, 58.5, 51.4, 51.3, 42.5, 42.4, 26.0, 25.9.

What is claimed is:

1. A radiological composition containing a compound of the formula:

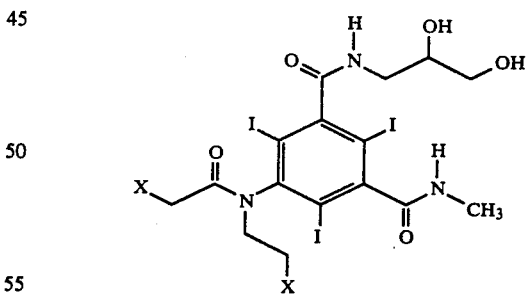

wherein the X groups may be the same or different selected from a group consisting of hydroxy and alkoxy containing from one to six carbon atoms, in an effective amount to provide satisfactory x-ray visualization together with a pharmaceutically acceptable radiological vehicle.

2. A radiological composition as set forth in claim 1 wherein said compound is N-(2,3-Dihydroxypropyl)-5-[N-(2-hydroxyethyl)-glycolamido]-N'-methyl-2,4,6-triiodoisophthalamide.

3. In a method for x-ray visualization wherein a radiological composition containing an x-ray contrast agent in a pharmaceutically acceptable radiological vehicle is administered in an effective amount to provide adequate visualization and thereafter x-ray visualization is carried out using as the radiological composition, a composition containing a compound of the formula:

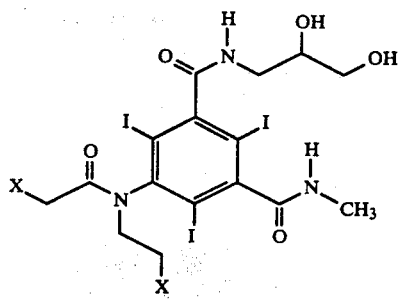

wherein the X groups may be the same or different selected from a group consisting of hydroxy and alkoxy containing from one to six carbon atoms.

4. A method as set forth to claim 3 wherein said compound is N-(2,3-Dihydroxypropyl)-5-[N-(2-hydroxyethyl)glycolamido]-N'-methyl-2,4,6-triiodoisophthalamide.

5. A compound of the formula:

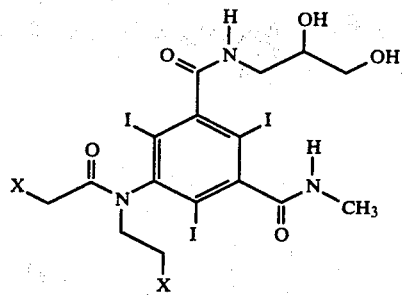

wherein the X groups may be the same or different selected from a group consisting of hydroxy and alkoxy containing from one to six carbon atoms.

6. A compound of claim 5 which is N-(2,3-Dihydroxypropyl)-5-[N-(2-hydroxyethyl)-glycolamido]-N'-methyl-2,4,6-triiodoisophthalamide.

* * * * *

UNITED STATES PATENT AND TRADEMARK OFFICE
CERTIFICATE OF CORRECTION

PATENT NO. : 5,019,371

DATED : May 28, 1991

INVENTOR(S) : Youlin Lin, Rebecca A. Wallace, David H. White

It is certified that error appears in the above-identified patent and that said Letters Patent is hereby corrected as shown below:

Column 2, line 22,
  "thyl)" should be --thyl)- --;

Column 2, line 34
  "hydroxyethyl)"should be --hydroxyethyl)- --;

Column 2, line 50
  "vehicle's" should be --vehicles--;

Column 2, line 62
  "agent" should be --agent.--

Column 4, line 25
  "bamoyl2" should be--bamoyl-2--;

Column 5   drawing

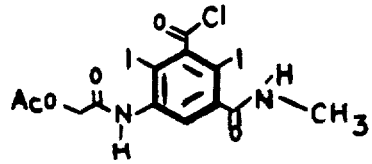

should be

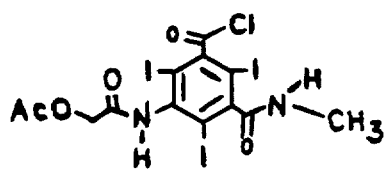

UNITED STATES PATENT AND TRADEMARK OFFICE
CERTIFICATE OF CORRECTION

PATENT NO. : 5,019,371

DATED : May 28, 1991

INVENTOR(S) : Youlin Lin, Rebecca A. Wallace, David H. White

Page 2 of 5

It is certified that error appears in the above-identified patent and that said Letters Patent is hereby corrected as shown below:

Column 5 drawing

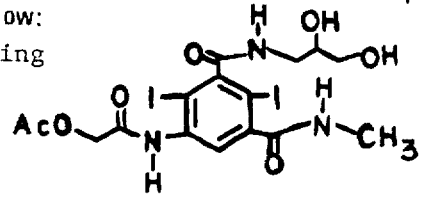

should be

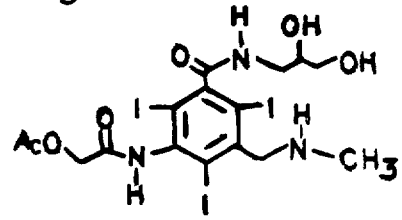

UNITED STATES PATENT AND TRADEMARK OFFICE
CERTIFICATE OF CORRECTION

PATENT NO. : 5,019,371
DATED : May 28, 1991
INVENTOR(S) : Youlin Lin, Rebecca A. Wallace, David H. White It is certified that error appears in the above-identified patent and that said Letters Patent is hereby corrected as shown below:

Column 6   drawing 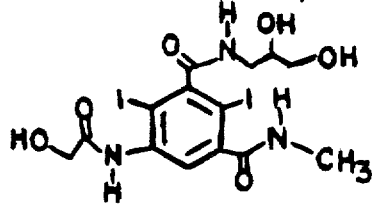

should be 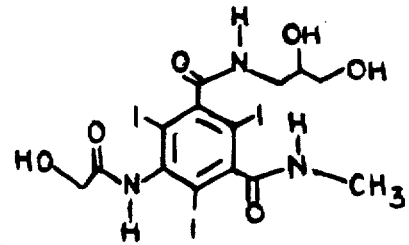

Column 6   drawing 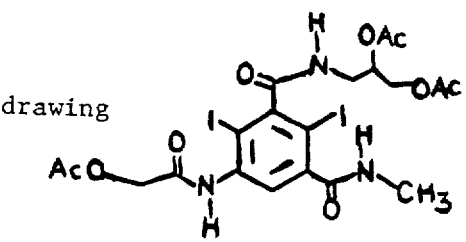

should be 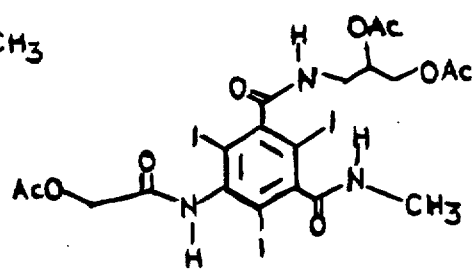

Column 7, line 6
  "acetoxyethylethyl" should be --acetoxyethyl--;

Column 7   drawing 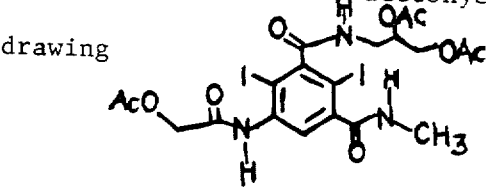

should be 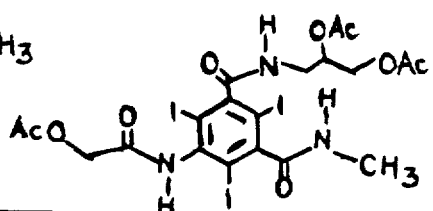

UNITED STATES PATENT AND TRADEMARK OFFICE
CERTIFICATE OF CORRECTION

PATENT NO. : 5,019,371

DATED : May 28, 1991

Page 4 of 5

INVENTOR(S) : Youlin Lin, Rebecca A. Wallace, David H. White

It is certified that error appears in the above-identified patent and that said Letters Patent is hereby corrected as shown below:

Column 7 drawing should be

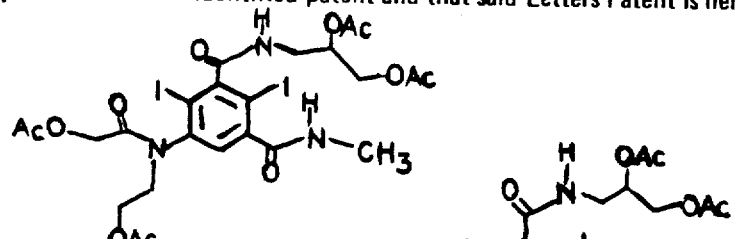

Column 8 drawing should be

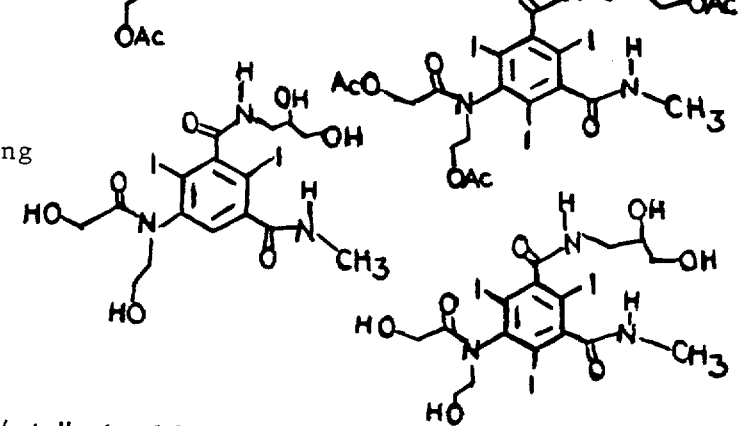

Column 8, line 34

"31.5 minutes: 1.7ml/min" should be --31.5 minutes; 1.7ml/min;

UNITED STATES PATENT AND TRADEMARK OFFICE
CERTIFICATE OF CORRECTION

PATENT NO. : 5,019,371
DATED : May 28, 1991
INVENTOR(S) : Youlin Lin, Rebecca A. Wallace, David H. White It is certified that error appears in the above-indentified patent and that said Letters Patent is hereby corrected as shown below:

Column 8, Line 37
        "71.6" should be --171.6.

Signed and Sealed this

Eighth Day of February, 1994

*Attest:*

BRUCE LEHMAN

*Attesting Officer*      *Commissioner of Patents and Trademarks*